United States Patent [19]

Chiodini et al.

[11] Patent Number: 4,920,099
[45] Date of Patent: Apr. 24, 1990

[54] AMINOGLYCOSIDE STEROIDS, A PROCESS FOR THEIR PREPARATION, THEIR USE AND PHARMACEUTICAL COMPOSITIONS CONTAINING THEM

[75] Inventors: Laura Chiodini, Busto Arsizio; Mauro Gobbini, Sesto Calende; Sergio Mantegani, Milan; Daniela Ruggieri, Milan; Aldemio Temperilli, Milan; Gabriella Traquandi, Cornate d'Adda; Patrizia Ferrari, Varese, all of Italy

[73] Assignee: Farmitalie Carlo Erba S.p.A., Milan, Italy

[21] Appl. No.: 123,855

[22] PCT Filed: Jan. 7, 1987

[86] PCT No.: PCT/EP87/00005
§ 371 Date: Oct. 29, 1987
§ 102(e) Date: Oct. 29, 1987

[87] PCT Pub. No.: WO87/04168
PCT Pub. Date: Jul. 16, 1987

[30] Foreign Application Priority Data

Jan. 9, 1986 [GB] United Kingdom ............... 8600490

[51] Int. Cl.$^5$ .................................. A61K 31/705
[52] U.S. Cl. .................................. 514/26; 536/5; 536/17.4; 536/18.7; 514/27
[58] Field of Search ............... 536/5, 6.2, 18.7, 17 A; 514/26, 27

[56] References Cited

U.S. PATENT DOCUMENTS

| | | | |
|---|---|---|---|
| 3,036,061 | 5/1962 | MacPhillamy | 536/5 |
| 3,451,994 | 6/1969 | Ferland et al. | 536/6.2 |
| 3,462,413 | 8/1969 | Ferland et al. | 536/5 |
| 3,914,213 | 10/1975 | Stache et al. | 536/6.2 |
| 4,088,757 | 5/1978 | Petersen | 514/26 |

FOREIGN PATENT DOCUMENTS

| | | | |
|---|---|---|---|
| 2915120 | 10/1979 | Fed. Rep. of Germany | 536/5 |
| 0004166 | 7/1987 | World Int. Prop. O. | 536/5 |

OTHER PUBLICATIONS

Lucas et al; J.A.C.S. 82: 5688–5693 (1960).
Katzung et al; Experientia 26(11): 1189–91 (1970).
Davisson et al; Chemical Abstracts 78: 119146c (1973).
Rohrer et al; J.A.C.S. 98(20): 6308–6312 (1976).
Makarevich et al; Chemical Abstracts 102: 185349m (1985).

Primary Examiner—Ronald W. Griffin
Assistant Examiner—Nancy S. Carson
Attorney, Agent, or Firm—Brooks Haidt Haffner & Delahunty

[57] ABSTRACT

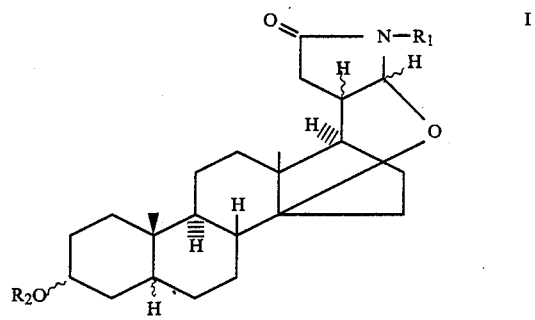

Compounds I [$R_1$=H or $C_1$-$C_3$ alkyl, $R_2$=an (alkyl-substituted) aminodeoxy or aminodideoxy or aminotrideoxy sugar residue of the D and L series, the glycosidic linkage being $\alpha$ or $\beta$] and their pharmaceutically acceptable salts are useful as antihypertensive agents. Their preparation and use as well as pharmaceutical compositions containing them are also described.

6 Claims, No Drawings

AMINOGLYCOSIDE STEROIDS, A PROCESS FOR THEIR PREPARATION, THEIR USE AND PHARMACEUTICAL COMPOSITIONS CONTAINING THEM

The invention relates to aminoglycoside steroids, to a process for their preparation and to pharmaceutical compositions containing them.

The invention provides aminoglycoside steroids having the general formula I

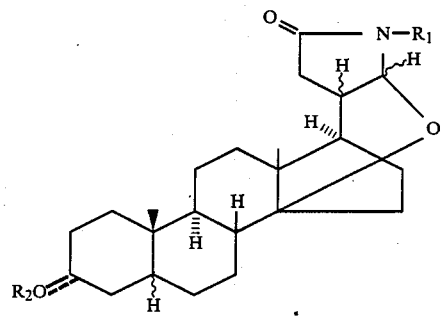

wherein $R_1$ represents a hydrogen atom, an optionally substituted alkyl group having from 1 to 3 carbon atoms and $R_2$ represents an optionally alkyl-substituted aminodeoxy, aminodideoxy or aminotrideoxy sugar residue of the D or L series. Such sugar residues are, for example, 2-amino or 2-alkylamino-2-deoxy-hexopyranosyl, 3-amino or 3-alkylamino-3-deoxy-hexopyranosyl, 3-amino or 3-alkyl-amino-3,6-dideoxy-hexopyranosyl, 3 amino or 3-alkylamino-2,3,6-trideoxy-hexopyranosyl, 4-amino or 4-alkylamino 2,4,6-trideoxy-hexopyranosyl residues of the D and L series.

The alkyl group $R_1$ may be the methyl, ethyl, i-propyl or n-propyl group. The substituents on the alkyl group which $R_1$ may represent are preferably of the formula —COOH, —COO—$C_1$-$C_4$ alkyl, $CONH_2$, $NH_2$, $NHCH_3$ or $N(CH_3)_2$.

The optional alkyl substituents of the sugar residue are preferably lower alkyl with $C_1$-$C_4$ atoms, e.g. methyl, ethyl, propyl and butyl. Advantageously the alkyl radicals may substitute the amino group of the sugar residue.

The wavy lines in above formula I indicate that the substituents or the hydrogen atoms may be above or under the plane of the ring system providing optically active isomer forms having different absolute configurations. These optically active forms either in the form of the racemate or as pure optical antipodes are encompassed by this invention. The racemates can be separated in accordance with methods known per se. Preferably the racemic mixture is reacted with an optically active separating agent to form diastereomers. As separating agents, e.g. optically active acids such as the D- and L- forms of tartaric acid, diacetyl-tartaric acid, dibenzoyl-tartaric acid, mandelic acid, malic acid, lactic acid or the various optically active camphersulfonic acids like β-camphersulfonic acid may be mentioned.

Of course, it is also possible to obtain optically active compounds of formula I in utilizing starting materials being optically active.

The glycosidic linkage can be α or β. Pharmaceutically acceptable salts of the compounds of the general formula I are also provided by the invention.

"Pharmaceutically acceptable salts" refers to those salts which retain the biological effectiveness and properties of the free bases and which are not biologically or otherwise undesirable. Such salts are formed with inorganic acids such as hydrochloric, hydrobromic, sulfuric, nitric or phosphoric acid and organic acids such as acetic, propionic, glycolic, pyruvic, oxalic, malic, malonic, succinic, maleic, fumaric, tartaric, citric, benzoic, cinnamic, mandelic, methanesulfonic, ethanesulfonic, p-toluene sulfonic or salicylic acid.

The invention further provides a process for the preparation of the aminoglycoside steroids of the general formula I as herein defined, which process comprises condensing a nor-cholane derivative having the general formula II

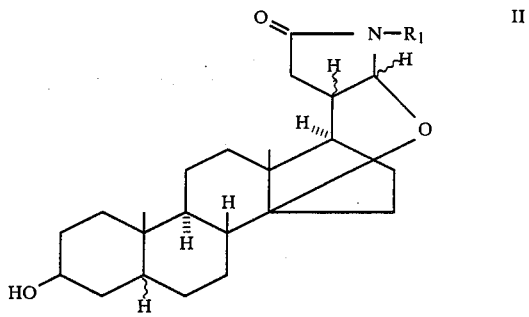

wherein $R_1$ has the above meaning with an optionally alkyl substituted, protected 1-halo derivative of an aminodeoxy, aminodideoxy or aminotrideoxy sugar of the D or L series, and removing the protecting groups from the resultant compound in a manner known per se. The removal can preferably be achieved with a base. The glycosidation process is desirably carried out in a suitable organic solvent such as chloroform or methylene dichloride in the presence of a catalyst. Particularly a soluble silver salt catalyst such as silver trifluoromethanesulphonate and of a molecular sieve as dehydrating agent at a temperature of from −5° C. to 25° C. provide good results. Reaction time may vary and conveniently be, e.g. one to eight hours.

The base used to remove the protecting groups is preferably potassium or sodium hydroxide. Treatment with the base may be effected for from two hours to three days.

The nor-cholane derivate of formula II and the aminodeoxy, aminodideoxy and aminotrideoxy sugars which may be alkylated used as starting materials are well known compounds or they may be prepared with procedures familiar to those skilled in the art.

The aminoglycoside steroids according to the invention and their pharmaceutically acceptable salts are capable of inhibiting specific ouabain binding without inhibiting Na+, K+-ATPase activity and thus they may be useful in pharmaceutical compositions, particularly in the treatment of hypertension. The compounds also can be used in the making of medicaments effective against hypertension.

'In vitro' assays to test the ability of aminoglycoside steroids of formula I to displace specific ouabain binding to the (Na+-K+)-ATPase receptors without inhibiting the (Na+-K+)-ATPase enzymatic activity.

Radiochemical assay:

A microsomial fraction enriched in $(Na^+-K^+)$-ATPase was prepared from dog kidney outer medulla, according to Jorgensen (BBA 356: 36-52, 1974).

The partially purified enzyme (0.5 μg of protein) was incubated in 3 mM $MgCl_2$, 3 mM EGTA, 80 mM Hepes buffer (pH 7.4) and 2 mM $y^2$ - $P^{32}$-ATP, final volume 110 μl, at 37° C. for 15 minutes with increasing concentrations of ouabain (as reference compound) or aminoglycoside steroids of the formula I.

The reaction was stopped by the addition of 0.1 mM of cold perchloric acid (10% final concentration) and 0.5 ml of charcoal suspension (20% w/v). The suspension was centrifuged and the content of $^{32}P$ in the supernatant was measured by liquid scintillation counting. (ref. Mall F. et al.; Biochem. Pharm. 33: N.1, 47-53, 1984).

The effects of various concentrations of aminoglycoside steroids and ouabain were expressed as a percentage of inhibition of the total $(Na^+-K^+)$-ATPase activity and $IC_{50}$ values were calculated. The compounds of the formula I according to the invention are inactive in this test.

Displacement of ouabain ($H^3$) binding from human red blood cells

The procedure has been described elsewhere (Erdmann E. et al.; Arzneim. Forsh 34(II), no. 10: 1314, 1984).

Washed erythrocytes (about $1-1.8 \times 10^9$/ml) were incubated in 130 mM NaCl, 1 mM $MgCl_2$, 10 mM glucose, 10 mM sucrose, 10 mM Tris/HCl buffer (pH 7.4) $2 \times 10^{-9}M$ $^3H$ ouabain and increasing concentration of the unlabelled aminoglycoside steroids, at 37° C. for 5 hours. Bound ouabain was quantitated by a rapid filtration technique (Whatman GF/C glass filter membranes; 'Whatman' is a Trade Mark) to separate free from membrane-bound ouabain. The radioactivity in the filters was determined by liquid scintillation counting. Non specific binding was defined as the binding in the presence of $10^{-3}M$ unlabelled ouabain.

The dissociation constant ($K_D$ value) was calculated from the concentration of unlabelled aminoglycoside steroids which inhibit $^3H$-ouabain binding by 50% at equilibrium, by the method of Erdmann et al. (Schmiedeberg's Arch. Pharmacol. 283: 335, 1973). The compounds of the formula I according to the invention are effective in this test with a $K_D$ value range of from $10^{-9}$ to $10^{-6}$.

Inhibition of $Na^+$ efflux mediated by the $(Na^+-K^+)$-ATPase in human red blood cells The procedure has been described elsewhere (Garay et al., Biochem Pharmacol. 33:2013-2020, 1984). Washed red blood cells were suspended to a hematocrit of 20-25% in 74 mM $MgCl_2$, 2 mM KCl, 84 mM sucrose, 10 mM MOPS/Tris buffer (pH 7.4 at 37° C.) and 10 mM glucose.

Red cell suspensions were added in the cold to tubes containing $Mg^{++}$ sucrose-$K^+$ medium with increasing concentration of ouabain and fixed concentrations of aminoglycoside steroids. The tubes were incubated at 37° C. and aliquots of the suspensions were transferred to the cold and spun down at different times (0-10-2-0-30 minutes). External $Na^+$ concentrations were measured in the supernatants by atomic absorption. A kinetic analysis of the inhibition of ouabain sensitive $Na^+$ efflux as a function of different aminoglycoside concentrations was done and the $IC_{50}$ for each compound was calculated.

The compounds of the formula I according to the invention are effective in a concentration range of from $10^{-9}$ to $10^{-6}M$.

'In vivo' assays to test the hypotensive activities of aminoglycoside steroids of formula I Indirect measurements of systolic blood pressure was carried out in groups of 4 spontaneously hypertensive rats (SHR.Kyoto), 8 to 10 weeks of age, supplied by Charles Rives, Italy. The animals were maintained in an environment of 36° C. for 10 to 15 minutes to allow pulse pressure to be recorded and then systolic blood pressure and heart rate were measured by the indirect tail cuff method using a W+W, BP recorder, model 8005. The compounds were given orally, suspended in 5% arabic gum, once a day for 4 consecutive days and measurements were carried out before beginning the treatment and 1 and 5 hours after dosing in both the first and fourth day of treatment. Control animals received the vehicle only (0.2 ml/100 g body weight). Drug induced changes in systolic blood pressure were calculated as differences from the pretreatment values.

The compounds of formula I are effective in a dosage range of from 0.01 to 100 mg/Kg.

These compounds can be used in form of pharmaceutical compositions in human or veterinary medicine. As the carrier substances organic or inorganic substances can be considered which are suitable for enteral (e.g. oral), parenteral or topical application and which do not react with the new compounds, for example water, vegetable oils, benzylalcohols, alkylenglycols, polyethyleneglycols, glycerinetriacetate, gelatin, carbohydrates such as lactose or starch, magnesium stearate, talc and vaseline. In particular for oral application tablets, pills, dragees, capsules, powders, granulates, syrups, juices or drops are used, for rectal application suppositories, for parenteral application solutions, preferably oily or aqueous solutions and furthermore suspensions, emulsions or implants, for the topical application salves, creams or powders are used. The new compounds can also be lyophilized and the lyophilisates thus obtained are used for example for the provision if injection preparations. The above mentioned preparations can be sterilized and/or can contain ancillary substances such as lubricant, conservation, stabilisation and/or wetting agents, emulsifiers, salts for influencing the osmotic pressure, buffer substances, colouring, taste-influencing and/or aromatic substances. If desired, they can also contain one or more other active ingredients, for example one or more vitamins.

The following Examples illustrate further preferred embodiments of the invention.

EXAMPLE 1

3-[(3-amino-3,6-dideoxy-α-L-altropyranosyl)oxy]-21-amino-14,21-epoxy-(3β,5β,14β,20S,21R)-24-nor-cholanic acid lactam.

To a mixture of 579 mg ($1.5 . 10^{-3}$ mole) of 21-amino-14,21-epoxy-3-hydroxy-(3β,5β,14β,20S,21R)-24-norcholanic acid lactam, 2 g of dried molecular sieves 4 Å and 1218 mg ($3 . 10^{-3}$ mole) of 3,6-dideoxy-2,4-di-O-acetyl-3-trifluoroacetamido-α-L-altropyranosyl bromide in 150 ml of dry dichloromethane, was added dropwise a solution of 768 mg ($3 . 10^{-3}$ mole) of silver trifluoromethanesulphonate in 50 ml of diethyl ether and the resulting mixture was stirred at 0° C. for 1 hour.

The silver salt was removed by filtration and the mixture washed with saturated aqueous sodium bicarbonate solution.

After anydrification (Na$_2$SO$_4$) and evaporation of the solvent, the crude product was chromatographed on silica gel column using acetone-hexane 1/5 as eluant affording 780 mg of the fully protected glycoside.

To a solution of 780 mg (1.17 . 10$^{-3}$ mole) of the above mentioned glycoside in 100 ml of methanol were added 8.45 ml (4.22 . 10$^{-3}$ mole) of a 0.5M solution of sodium hydroxide in methanol/water 9/1 and the mixture was stirred at room temperature for 3 days. The solvent was evaporated off and the residue was dissolved in dichloromethane and washed with brine.

After anydrification (Na$_2$SO$_4$), evaporation of the organic solvent, the remaining material was crystallized from methanol giving 430 mg of the title compound, m.p. 215°–217° C.

EXAMPLE 2

3-[(3-amino-3,6-dideoxy-α-L-altropyranosyl)oxy]-21-amino-14,21-epoxy-(3β,5β,14β,20R,21S)-24-nor-cholanic acid lactam.

Operating as in Example 1, but employing 21-amino-14,21-epoxy-3-hydroxy-(3β,5β,14β,20R,21S)-24-nor-cholanic acid lactam, the title compound was obtained in 55% yield, m.p. 233°–235° C.

EXAMPLE 3

3-[(3-amino-3,6-dideoxy-α-D-altropyranosyl)oxy]-21-amino-14,21-epoxy-(3β,5β,14β,20S,21R)-24-nor-cholanic acid lactame.

Operating as in Example 1, but employing 3,6-dideoxy-2,4-di-O-acetyl-3-trifluoroacetamido-α-D-altropyranosyl bromide, the title compound was obtained in 57% yield, m.p.280°–284° C.

EXAMPLE 4

3-[(3-amino-3,6-dideoxy-α-D-altropyranosyl)oxy]-21-amino-14,21-epoxy-(3β,5β,14β,20R,21S)-24-nor-cholanic acid lactam.

Operating as in Example 2, but employing 3,6-dideoxy-2,4-di-O-acetyl-3-trifluoroacetamido-α-D-altropyranosylbromide, the title compound was obtained in 60% yield , m.p.202°–204° C.

EXAMPLE 5

3-(3,6-dideoxy-3-dimethylamino-α-L-altropyranosyl)oxy]-21-amino-14,21-epoxy-(3β,5β,14β,20S,21R)-24-nor-cholanic acid lactam.

Operating as in Example 1, but employing 3,6-dideoxy-3-dimethylamino-2,4-di-O-acetyl-α-L-altropyranosyl bromide hydrobromide, the title compound was obtained in 62% yield.

EXAMPLE 6

3-[(3,6-dideoxy-3-dimethylamino-α-L-altropyranosyl)oxy]-21-amino-14,21-epoxy-(3β,5β,14β,20R,21S)-24-nor-cholanic acid lactam.

Operating as in Example 2, but employing 3,6-dideoxy-3-dimethylamino-2,4-di-O-acetyl-α-L-altropyranosyl bromide hydrobromide, the title compound was obtained in 58% yield.

EXAMPLE 7

3-[(3,6-dideoxy-3-dimethylamino-α-D-altropyranosyl)oxy]-21-amino-14,21-epoxy-(3β,5β,14β,20S,21R)-24-nor-cholanic acid lactam.

Operating as in Example 1, but employing 3,6-dideoxy-3-dimethylamino-2,4-di-O-acetyl-α-D-altropyranosyl bromide hydrobromide, the title compound was obtained in 60% yield.

EXAMPLE 8

3-[(3,6-dideoxy-3-dimethylamino-α-D-altropyranosyl)oxy]-21-amino-14,21-epoxy-(3β,5β,14β,20R,21S)-24-nor-cholanic acid lactam.

Operating as in Example 2, but employing 3,6-dideoxy-3-dimethylamino-2,4-di-O-acetyl-α-D-altropyranosyl bromide hydrobromide, the title compound was obtained in 61% yield.

EXAMPLE 9

3-[3-amino-3-deoxy-α-D-mannopyranosyl)oxy]-21-amino-14,21-epoxy-(3β,5β,14β,20S,21R)-24-nor-cholanic acid lactam.

Operating as in Example 1, but employing 3-deoxy-2,4,6-tri-O-acetyl-3-trifluoroacetamido-α-D-mannopyranosyl bromide, the title compound was obtained in 50% yield, m.p.278–280° C.

EXAMPLE 10

3-amino-3-deoxy-α-D-mannopyranosyl)oxy]-21-amino-14,21-epoxy-(3β,5β,14β,20R,21S)-24-nor-cholanic acid lactam.

Operating as in Example 2, but employing 3-deoxy-2,4,6-tri-O-acetyl-3-trifluoroacetamido-α-D-mannopyranosyl bromide, the title compound was obtained in 56% yield , m.p.267–269° C.

EXAMPLE 11

3-3-amino-3-deoxy-α-L-mannopyranosyl)oxy]-21-amino-14,21-epoxy-(3β,5β,14β,20S,21R)-24-nor-cholanic acid lactam.

Operating as in example 1, but employing 3-deoxy-2,4,6-tri-O-acetyl-3-trifluoroacetamido-α-L-mannopyranosylbromide, the title compound was obtained in 52% yield.

EXAMPLE 12

3-[3-amino-3-deoxy-α-L-mannopyranosyl)oxy]-21-amino-14,21-epoxy-(3β,5β,14β,20R,21S)-24-nor-cholanic acid lactam.

Operating as in Example 2, but employing 3-deoxy-2,4,6-tri-O-acetyl-3-trifluoroacetamido-α-L-mannopyranosyl bromide, the title compound was obtained in 50% yield.

EXAMPLE 13

3-[3-amino-3,6-dideoxy-α-D-mannopyranosyl)oxy]-21-amino-14,21-epoxy-(3β,5β,14β,20S,21R)-24-nor-cholanic acid lactam.

Operating as in Example 1, but employing 2,4-di-O-acetyl-3,6-dideoxy-3-trifluoroacetamido-α-D-mannopyranosyl bromide, the title compound was obtained in 55% yield, m.p.263°–265° C.

EXAMPLE 14

3-[3-amino-3,6-dideoxy-α-D-mannopyranosyl)-oxy-]-21-amino-14.21-epoxy-(3β,5β,14β,20R,21S)-24-nor-cholanic acid lactam.

Operating as in Example 2, but employing 2,4-di-O-acetyl-3,6-dideoxy-3-trifluoroacetamido-α-D-mannopyranosyl bromide, the title compound was obtained in 58% yield.

EXAMPLE 15

3[3-amino-3,6-dideoxy-α-L-mannopyranosyl)oxy]21-amino-14,21-epoxy-(3β,5β,14β,20S,21R)-24-nor-cholanic acid lactam.

Operating as in Example 1, but employing 2,4-di-O-acetyl-3,6-dideoxy-3-trifluoroacetamido-α-L-mannopyranosyl bromide, the title compound was obtained in 54% yield, m.p. 287°–289° C.

EXAMPLE 16

3[3-amino-3,6-dideoxy-α-L-mannopyranosyl-oxy]21-amino-14,21-epoxy-(3β,5β,14β,20R,21S)-24-nor-cholanic acid lactam.

Operating as in example 2, but employing 2,4-di-O-acetyl-3,6-dideoxy-3-trifluoroacetamido-β-L-mannopyranosyl bromide, the title compound was obtained in 60% yield.

EXAMPLE 17

3-(3-amino-2,3,6-trideoxy-α-L-lyxo-hexopyranosyl)oxy]-21-amino14,21-epoxy-(3β,5β,14β,20S,21R)-24-nor-cholanic acid lactam.

Operating as in Example 1, but employing 2,3,6-trideoxy-3-trifluoroacetamido-4-O-trifluoroacetyl-β-L-lyxo-hexopyranosyl chloride, a mixture of α and β-glycosides was obtained in 65% yield. The title compound was isolated by crystallization from diethyl ether-methanol in 33% yield, m.p. 178°–180° C.

EXAMPLE 18

3-[(3-amino-2,3,6-trideoxy-β-L-lyxo-hexopyranosyl)oxy]-21-amino-14,21-epoxy-(3β,5β,14β,20S,21R)-24-nor-cholanic acid lactam.

The residue of the mother liquors obtained in Example 17 was crystallized from diethyl ether, affording the title compound in 30% yield, m.p. 163°–165° C.

EXAMPLE 19

3-[(3-amino-2,3,6-trideoxy-α-L-lyxo-hexopyranosyl)oxy]-21-amino-14,21-epoxy-(3β,5β,14β,20R,21S)-24-nor-cholanic acid lactam.

Operating as in Example 2, but employing 2,3,6-trideoxy-3-trifluoroacetamido-4-O-trifluoroacetyl-α-L-lyxo-hexopyranosyl chloride, a mixture of α and β-glycosides was obtained in 70% yield.
The title compound was isolated by crystallization from methanol in 34% yield, m.p 204°–207° C.

EXAMPLE 20

3[-(3-amino-2,3,6-trideoxy-β-L-lyxo-hexopyranosyl)oxy-21-amino-14,21-epoxy-(3β,5β,14β,20R,21S)-24-nor-cholanic acid lactam.

The residue of the mother liquors obtained in Example 19 was crystallized from diethyl ether-methanol, affording the title compound in 32% yield, m.p. 243°–245° C.

EXAMPLE 21

3-[3-amino-2,3,6-trideoxy-α-D-lyxo-hexopyranosyl)oxy]-21-amino-14,21-epoxy-(3β,5β,14β,20S,21R)-24-nor-cholanic acid lactam.

Operating as in Example 1, but employing 2,3,6-trideoxy-3-trifluoroaetamido-4-O-trifluoroacetyl-α-D-lyxo-hexopyranosyl chloride, a mixture of α and β-glycosides was obtained in 63% yield. The title compound was isolated by crystallization from cyclohexane-diethyl ether in 28% yield, m.p.251°–253° C.

EXAMPLE 22

3-[(3-amino-2,3,6-trideoxy-β-D-lyxo-hexopyranosyl)oxy]-21-amino-14,21-epoxy-(3β,5β,14β,20S,21R)-24-nor-cholanic acid lactam.

The residue of the mother liquors obtained in Example 21 was crystallized from diethyl ether, affording the title compound in 32% yield, m.p. 254°–256° C.

EXAMPLE 23

3-[(3-amino-2,3,6-trideoxy-α-D-lyxo-hexopyranosyl)oxy]-21-amino-14,21-epoxy-(3β,5β,14β,20R,21S)-24-nor-cholanic acid lactam.

Operating as in Example 2, but employing 2,3,6-trideoxy-3-trifluoroacetamido-4-O-trifluoroacetyl-α-D-lyxo-hexopyranosyl chloride, a mixture of α and β-glicosides was obtained in 68% yield. The title compound was isolated by crystallization from ethanol in 35% yield, m.p. 238°–241° C.

EXAMPLE 24

3-[(3-amino-2,3,6-trideoxy-β-D-lyxo-hexopyranosyl)oxy]-21-amino-14,21-epoxy-(3β,5β,14β,20R,21S)-24-nor-cholanic acid lactam.

The residue of the mother liquors obtained in Example 23 was crystallized from diethyl ether-ethanol, affording the title compound in 30% yield, m.p. 181°–184° C.

EXAMPLE 25

3-[(3-amino-2,3,6-trideoxy-α-L-arabino-hexopyranosyl)oxy]-21-amino-14,21-epoxy-(3β,5β,14β,20S,21R)-24-nor-cholanic acid lactam.

Operating as in Example 1, but employing 2,3,6-trideoxy-3-trifluoroacetamido-4-O-trifluoroacetyl-α-L-arabino-hexopyanosyl chloride, a mixture of α and β-glycosides was obtained in 60% yield. The title compound was isolated by crystallization from methanol in 25% yield, m.p. 268°–270° C.

EXAMPLE 26

3-[(3-amino-2,3,6-trideoxy-β-L-arabino-hexopyranosyl)oxy]-21-amino-14,21-epoxy-(3β,5β,14β,20S,21R)-24-nor-cholanic acid lactam.

The residue of the mother liquors obtained in Example 25 was crystallized from diethyl ether-methanol, affording the title compound in 25% yield.

EXAMPLE 27

3-[(3-amino-2,3,6-trideoxy-α-L-arabino-hexopyranosyl)oxy]-21-amino-14,21-epoxy-(3β,5β,14β,20R,21S)-24-nor-cholanic acid lactam.

Operating as in Example 2, but employing 2,3,6-trideoxy-3-trifluoroacetamido-4-O-trifluoroacetyl-β-L-arabino-hexopyra nosyl chloride, a mixture of α and β-glycosides was obtained in 65% yield. The title compound was isolated by crystallization from methanol in 35% yield.

EXAMPLE 28

3-[(3-amino-2,3,6-trideoxy-β-L-arabino-hexopyranosyl)oxy]-21-amino-14,41-epoxy-(3β,5β,14β,20R,21S)-24-nor-cholanic acid lactam.

The residue of the mother liquors obtained in Example 27 was crystallized from diethyl ether-ethanol, affording the title compound in 25% yield.

EXAMPLE 29

3-[(3-amino-2,3,6-trideoxy-α-D-arabino-hexopyranosyl)oxy]-21-amino-14,21-epoxy-(3β,5β,14β,20S,21R)-24-nor-cholanic acid lactam.

Operating as in Example 1, but employing 2,3,6-trideoxy-3-trifluoroacetamido-4-O-trifluoroacetyl-β-D-arabino-hexopyranosyl chloride, a mixture of α and β-glycosides was obtained in 70% yield. The title compound was isolated by crystallization from methanol in 30% yield, m.p. 246°-248° C.

EXAMPLE 30

3-[(3-amino-2,3,6-trideoxy-β-D-arabino-hexopyranosyl)oxy]-21-amino-14,21-epoxy-(3β,5β,14β,20S,21R)-24-nor-cholanic acid lactam.

The residue of the mother liquors obtained in Example 29 was crystallized from diethyl ether, affording the title compound in 27% yield.

EXAMPLE 31

3-[(3-amino-2,3,6-trideoxy-α-D-arabino-hexopyranosyl)oxy]-21-amino-14,21-epoxy-(3β,5β,14β,20R,21S)-24-nor-cholanic acid lactam.

Operating as in Example 2, but employing 2,3,6-trideoxy-3-trifluoroacetamido-4-O-trifluoroacetyl-α-D-arabino-hexopyranosyl chloride, a mixture of α and β-glycosides was obtained in 63% yield. The title compound was isolated by crystallization from ethanol in 27% yield, m.p.282°-284° C.

EXAMPLE 32

3-[(3-amino-2,3,6-trideoxy-β-D-arabino-hexopyranosyl)oxy]-21-amino-14,21-epoxy-(3β,5β,14β,20R,21S)-24-nor-cholanic acid lactam.

The residue of the mother liquor obtained in Example 31 was crystallized from diethyl ether, affording the title compound in 30% yield , m.p. 202°-204° C.

EXAMPLE 33

3-[(3-amino-3-deoxy-β-D-glucopyranosyl)oxy]-21-amino-14,21-epoxy-(3β,5β,14β,20S,21R)-24-nor-cholanic acid lactam.

Operating as in Example 1 but employing 3-deoxy-2,4,6-tri-O-acetyl-3-trifluoroacetamido-α-D-glucopyranosyl bromide, the title compound was obtained in 60% yield, m.p.295°-300° C.

EXAMPLE 34

3-[(3-amino-3-deoxy-β-D-glucopyranosyl)oxy]-21-amino-14,21-epoxy-(3β,5β,14β,20R,21S)-24-nor-cholanic acid lactam.

Operating as in Example 2 but employing 3-deoxy-2,4,6-tri-O-acetyl-3-trifluoroacetamido-α-D-glucopyranosyl bromide, the title compound was obtained in 55% yield,m.p.270°-280° C.

EXAMPLE 35

3-[(3-amino-3-deoxy-β-D-allopyranosyl)oxy]-21-amino-14,21-epoxy-(3β,5β,14β,20S,21R)-24-nor-cholanic acid lactam.

Operating as in Example 1 but employing 3-deoxy-2,4,6-tri-O-acetyl-3-trifluoroacetamido-α-D-allopyranosyl bromide, the title compound was obtained in 42% yield.

EXAMPLE 36

3-[(3-amino-3-deoxy-β-D-allopyranosyl)oxy]-21-amino-14,21-epoxy-(3β,5β,14β,20R,21S)-24-nor-cholanic acid lactam.

Operating as in Example 2 but employing 3-deoxy-2,4,6-tri-O-acetyl-3-trifluoroacetamido-α-D-allopyranosyl bromide, the title compound was obtained in 39% yield.

EXAMPLE 37

3-[(3-deoxy-3-dimethylamino-β-D-glucopyranosyl)oxy]-21-amino-14,21-epoxy-(3β,5β,14β,20S,21R)-24-nor-cholanic acid lactam.

Operating as in Example 1 but employing 3-deoxy-3-dimethylamino-2,4,6-tri-O-acetyl-α-D-glucopyranosyl bromide, the title compound was obtained in 57% yield.

EXAMPLE 38

3-[(3-deoxy-3-dimethylamino-β-D-glucopyranosyl)oxy]-21-amino-14,21-epoxy-(3β,5β,14β,20R,21S)-24-nor-cholanic acid lactam.

Operating as in Example 2 but employing 3-deoxy-3-dimethyl amino-2,4,6-tri-O-acetyl-α-glucopyranosyl bromide, the title compound was obtained in 53% yield.

EXAMPLE 39

3-[(2-amino-2-deoxy-β-D-glucopyranosyl)oxy]-21-amino-14,21-epoxy-(3β,5β,14β,20S,21R)-24-nor-cholanic acid lactam.

Operating as in Example 1 but employing 2-deoxy-3,4,6-tri-O-acetyl-2-trifluoroacetamido-α-D-glucopyranosyl bromide, the title compound was obtained in 52% yield.

EXAMPLE 40

3-[(2-amino-2-deoxy-β-D-glucopyranosyl)oxy]-21-amino-14,21-epoxy-(3β,5β,14β,20R,21S)-24-nor-cholanic acid lactam.

Operating as in Example 2 but employing 2-deoxy-3,4,6-tri-O-acetyl-2-trifluoroacetamido-α-D-glucopyranosyl bromide, the title compound was obtained in 37% yield.

EXAMPLE 41

3-[(3-amino-3-deoxy-β-L-glucopyranosyl)oxy]-21-amino-14,21-epoxy-(3β,5β,14β,20S,21R)-24-nor-cholanic acid lactam.

Operating as in Example 1 but employing 3-deoxy-2,4,6-tri-O-acetyl-3-trifluoroacetamido-α-L-glucopyranosyl bromide, the title compound was obtained in 61% yield.

EXAMPLE 42

3-[(3-amino-3-deoxy-β-L-glucopyranosyl)oxy]-21-amino-14,21-epoxy-(3β,5β,14β,20R,21S)-24-nor-cholanic acid lactam.

Operating as in Example 2 but employing 3-deoxy-2,4,6-tri-O-acetyl-3-trifluoroacetamido-α-L-glucopyranosyl bromide, the title compound was obtained in 58% yield.

EXAMPLE 43

3-[(3-amino-3-deoxy-β-L-allopyranosyl)oxy]-21-amino-14,21-epoxy-(3β,5β,14β,20S,21R)-24-nor-cholanic acid lactam.

Operating as in Example 1 but employing 3-deoxy-2,4,6-tri-O-acetyl-3-trifluoroacetamido-α-L-allopyranosyl bromide, the title compound was obtained in 44% yield.

EXAMPLE 44

3-[(3-amino-3-deoxy-β-L-allopyranosyl)oxy]-21-amino-14,21-epoxy-(3β,5β,14β,20R,21S)-24-nor-cholanic acid lactam.

Operating as in Example 2, but employing 3-deoxy-2,4,6-tri-O-acetyl-3-trifluoroacetamido-α-L-allopyranosyl bromide, the title compound was obtained in 41% yield.

EXAMPLE 45

3-[(3-amino-3,6-dideoxy-α-L-altropyranosyl)oxy]-21-(3-dimethylaminopropyl)amino-14,21-epoxy-(3β,5β,14β,20S,21R)-24-nor-cholanic acid lactam.

Operating as in Example 1, but employing 21-(3-dimethylaminpropyl)amino-14,21-epoxy-3-hydroxy-(3β,5β,14β,20S,21R)-24-nor cholanic acid lactam, the title compound was obtained in 65% yield, m.p. 142°–145° C.

EXAMPLE 46

3-[(3-amino-3,6-dideoxy-α-L-altropyranosyl)oxy]-21-(3-dimethylaminopropyl)amino-14,21-epoxy-(3β,5β,14β,20R,21S)-24-nor-cholanic acid lactam.

Operating as in Example 1, but employing 21-(3-dimethylaminopropyl)amino-14,21-epoxy-(3β,5β,14β,20R,21S)-24-nor-cholanic acid lactam, the title compound was obtained in 70% yield, m.p. 148°–150° C.

EXAMPLE 47

3-[(3-amino-3,6-dideoxy-α-L-altropyranosyl)oxy]-21-amino-14,21-epoxy-(3α,5β,14β,20S,21R)-24-nor-cholanic acid lactam.

Operating as in Example 1, but employing 21-amino-14,21-epoxy-3-hydroxy-(3α,5β,14β,20S,21R)-24-nor-cholanic acid lactam, the title compound was obtained in 65% yield, m.p. 182°–185° C.

EXAMPLE 48

3-[2-amino-2-deoxy-β-D-glucopyranosyl)oxy]-21-amino-14,21-epoxy-(3β,5β,14β,20S,21R)-24-nor-cholanic acid lactam.

Operating as in Example 1, but employing 2-deoxy-2-diphenylposphorylamino-3,4,6-O-acetyl-β-D-glucopyranosyl bromide, the title compound was obtained in 70% yield, m.p. 192°–194° C.

EXAMPLE 49

3-[(4-amino-2,4,6-trideoxy-α-L-lyxo-hexopyranosyl)oxy]-21-amino-14,21-epoxy-(3β,5β,14β,20S,21R)-24-nor-cholanic acid lactam.

Operating as in Example 1, but employing 2,4,6-trideoxy-4-trifluoroacetamido-α-L-lyxo-hexopyranosyl chloride, the title compound was obtained in 63% yield, m.p. 274°–276° C.

EXAMPLE 50

3-[(amino-3,6-dideoxy-α-D-mannopyranosyl)oxy-]-21-amino-14,21-epoxy-(3α,5β,14β,20S,21R)-24-nor-cholanic acid lactam.

Operating as in Example 1, but employing 21-amino-14,21-epoxy-3-hydroxy-(3α,5β,14β,20S,21R)-24-nor-cholanic acid lactam and 3,6-dideoxy-3-trifluoroacetamido-2,4-di-O-benzoyl-α-D-mannopyranosyl bromide, the title compound was obtained in 50% yield, m.p.265°–267° C.

EXAMPLE 51

3-[(3-(amino-2,3,6-trideoxy-α-D-arabino-hexopyranosyl)oxy]-21-amino-14,21-epoxy-(3β,5β,14β,20S,21R)-24-nor-cholanic acid lactam.

Operating as in Example 1, but employing 21-amino-14,21-epoxy-3-hydroxy-(3β,5β,14β,20S,21R)-24-nor-cholanic acid lactam and 2,3,6-tridoexy-3-trifluoroacetamido-4-O-trifluoroacetyl-α-D-arabino-hexopyranosyl chloride, the title compound was obtained in 45% yield, m.p. 192°–196° C.

EXAMPLE 52

Tablets of 3-[(3-amino-3,6-dideoxy-α-L-altropyranosyl)oxy]-21-amino-14,21-epoxy-(3β,5β,14β,20S,21R)-24-nor-cholanic acid lactam Tablets of compound of Example 1 were produced in the following way: 50 g of the title compound, 132 g of lactose and 6 g acacia were mixed. Purified water was then added to the mixture, whereupon the mixing was continued until a suitable consistency was obtained. The mixture was sieved and dried. After the blending with 10 g talcum and 2 g magnesium stearate the mixture was compressed into tablets each weighing 200 mg.

We claim:

1. A compound and the pharmaceutically acceptable salts of said compound having the general formula I

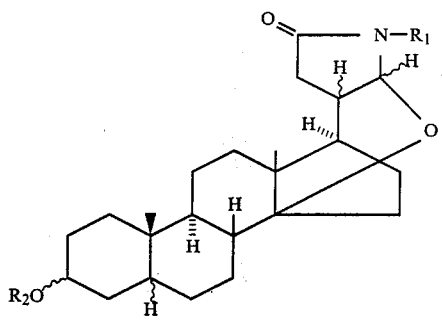

wherein $R_1$ represents a hydrogen atom, an alkyl group having from 1 to 3 carbon atoms or an alkyl group substituted by an amino, methylamino, dimethylamino, carbamoyl, carboxy or carboxy-$C_1$–$C_4$ alkyl group; and $R_2$ represents an aminodeoxy, aminodideoxy, or aminotrideoxy mono- or di-saccharide of the D or L series, or a $C_1$–$C_4$ alkyl substituted aminodeoxy, aminodideoxy or aminotrideoxy mono- or di-saccharide, of the D or L series.

2. A compound and the pharmaceutically acceptable salts of said compound according to claim 1 wherein the mono- or disaccharide is $C_1$–$C_4$ alkyl-substituted.

3. A compound and the pharmaceutically acceptable salts of said compound according to claim 1 in which the mono- or disaccharide is a 2-amino or 2-alkylamino-2-deoxy-hexo pyranosyl, 3-amino-3-deoxyhexopyranosyl, 3-amino or 3-alkylamino-3,6-dideoxy-hexopyranosyl, 3-amino or 3-alkylamino-2,3,6-trideoxy-hexopyranosyl or 4-amino or 4-alkylamino-2,4,6-trideoxy-hexopyranosyl residue of the D or L series.

4. 3-[(3-amino-2,3,6-trideoxy-alpha-D-arabinohexopyranosyl)oxy]-21-amino-14,21-epoxy-(3 beta, 5 beta, 14 beta, 20S, 21R)-24-nor-cholanic acid lactam.

5. A pharmaceutical composition comprising:

a compound or a pharmaceutically acceptable salt of said compound having the general formula I

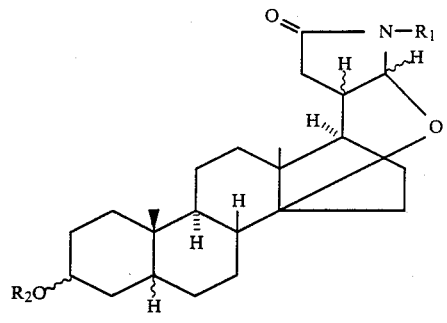

wherein $R_1$ represents a hydrogen atom, an alkyl group having from 1 to 3 carbon atoms or an alkyl group substituted by an amino, methylamino, dimethylamino, carbamoyl, carboxy or carboxy-$C_1$–$C_4$ alkyl group; and $R_2$ represents an aminodeoxy, aminodideoxy, or aminotrideoxy mono- or di-saccharide of the D or L series, or a $C_1$–$C_4$ alkyl substituted aminodeoxy, aminodideoxy or aminotrideoxy mono- or di-saccharide, of the D or L series, in admixture with a pharmaceutically acceptable diluent or carrier.

6. A method for treating hypertension which comprises administering to a subject either (a) an effective amount of a compound or a pharmaceutically acceptable salt of said compound having the general formula I

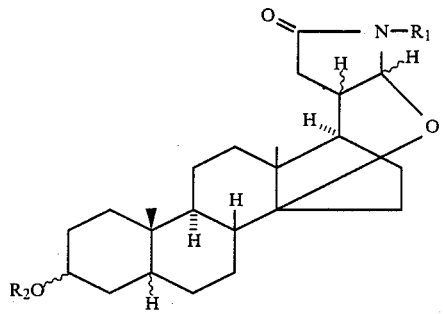

wherein $R_1$ represents a hydrogen atom, an alkyl group having from 1 to 3 carbon atoms or an alkyl group substituted by an amino, methylamino, dimethylamino, carbamoyl, carboxy or carboxy-$C_1$–$C_4$ alkyl group; and $R_2$ represents an aminodeoxy, aminodideoxy, or aminotrideoxy mono- or di-saccharide, of the D or L series, or a $C_1$–$C_4$ alkyl substituted aminodeoxy, aminodideoxy or aminotrideoxy mono- or di-saccharide, of the D or L series, or (b) an effective amount of the compound or pharmaceutically acceptable salt of said compound having the general formula I in admixture with a pharmaceutically acceptable diluent or carrier.

* * * * *